US007272429B2

(12) United States Patent
Walker et al.

(10) Patent No.: US 7,272,429 B2
(45) Date of Patent: Sep. 18, 2007

(54) METHODS AND APPARATUS FOR FACILITATING A REDUCTION IN ARTIFACTS

(75) Inventors: Matthew Joseph Walker, New Berlin, WI (US); John Michael Sabol, Sussex, WI (US); Gopal B. Avinash, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 719 days.

(21) Appl. No.: 10/306,197

(22) Filed: Nov. 27, 2002

(65) Prior Publication Data

US 2004/0102688 A1 May 27, 2004

(51) Int. Cl.
*A61B 5/05* (2006.01)
(52) U.S. Cl. .............................. 600/407; 378/4; 378/5; 382/131
(58) Field of Classification Search ................ 600/425, 600/407; 378/4, 5; 382/131
See application file for complete search history.

(56) References Cited

U.S. PATENT DOCUMENTS

| 4,029,963 | A |   | 6/1977  | Alvarez et al.  |          |
|-----------|---|---|---------|-----------------|----------|
| 4,361,901 | A | * | 11/1982 | Daniels et al.  | 378/106  |
| 4,709,333 | A | * | 11/1987 | Crawford        | 600/425  |
| 4,792,900 | A | * | 12/1988 | Sones et al.    | 600/407  |
| 5,115,394 | A |   | 5/1992  | Walters         |          |
| 6,418,189 | B1 |   | 7/2002 | Schafer         |          |
| 6,661,873 | B2 | * | 12/2003 | Jabri et al.   | 378/98.11 |
| 6,748,098 | B1 | * | 6/2004 | Rosenfeld      | 382/131  |
| 2004/0101090 | A1 | * | 5/2004 | Drummond et al. | 378/4 |
| 2004/0136491 | A1 | * | 7/2004 | Iatrou et al.   | 378/4 |

OTHER PUBLICATIONS

"Techniques to Alleviate the Effects of View Aliasing Artifacts in Computed Tomography," Galigekere, et al., *Med. Phys.* 26(6), Jun. 1999.
"Energy-Selective Reconstructions in X-ray Computerized Tomography," Alvarez, et al., *Phys. Med. Biol.*, 1976, vol. 21, No. 5, 733-744.
"Lung Nodules: Dual-Kilovolt Peak Analysis with CT—Multicenter Study," Swensen, et al., *Radiology*, Jan. 2000.
Dual-Kilovolt CT of Solitary Pulmonary Nodules: Importance of Equipment Calibration and Soft-Tissue Controls, PANDIT-BHALLA, *Radiology*, Jan. 2001.

* cited by examiner

*Primary Examiner*—Eleni Mantis Mercader
*Assistant Examiner*—Jacqueline Cheng
(74) *Attorney, Agent, or Firm*—Armstrong Teasdale LLP (57) ABSTRACT

A method for facilitating a reduction in artifacts includes receiving data regarding a first energy spectrum of a scan of an object, and receiving data regarding a second energy spectrum of a scan of the object, wherein the second energy spectrum is different than the first energy spectrum. The method further includes reconstructing at least one original first energy image using the first energy spectrum data, reconstructing at least one original second energy image using the second energy spectrum data, transforming at least one original second energy image into at least one transformed first energy image, and combining at least one original first energy image with at least one transformed first energy image to generate a combined first energy image.

21 Claims, 4 Drawing Sheets

FIG. 3  Plot of two tungsten anode x-ray spectra

METHODS AND APPARATUS FOR FACILITATING A REDUCTION IN ARTIFACTS

BACKGROUND OF THE INVENTION

This invention relates generally to the acquisition and processing of multi-energy computed tomographic data, and more particularly to methods and apparatus for simultaneous spectral-shift and view-aliasing artifact compensations.

In spite of recent advancements in computed tomography (CT) technology, such as faster scanning speeds, larger coverage with multiple detector rows, and thinner slices, energy resolution is still a missing piece. Conventional CT images represent the x-ray attenuation of an object under investigation. Strictly speaking, this definition is not correct, due to the wide x-ray photon energy spectrum from the x-ray source and the lack of energy resolution from detection system used in the conventional CT systems. X-ray attenuation through a given object is not a constant. Rather the X-ray attenuation is strongly dependent on the x-ray photon energy.

The attenuation at a specific point is generally greater for photons of lower energy and causes the energy spectrum to shift as it passes through the body. X-ray beams reaching a particular point inside the body from different directions will typically have different spectra since they passed through materials with different attenuation properties before reaching that point. This creates challenges when attempting to assign a single value to the attenuation at a specific point in the scanned body. This physical phenomenon manifests itself in the image as beam-hardening artifacts such as non-uniformity, shading, and streaks. The visual conspicuity of some of these artifacts can be reduced, but some are much tougher to remove. By filtering the pre-patient beam with an aluminum or copper filter, the lower-energy components of the spectrum can be selectively removed. This lessens the effects of beam hardening effects, but cannot wholly remove these effects. Additionally, there is also a practical limit to the amount of filtration that may be performed. Filtration reduces the total energy flux, which results in an increase in noise. Additionally, the loss of lower energy photons reduces the contrast discrimination.

The literature is rich in beam-hardening correction algorithms that serve to augment filtration. For scans of predominantly soft-tissue anatomy with x-ray spectra and peak kilovoltages typically used for medical CT, beam hardening effects are almost entirely due to Compton scattering. For single energy scanning, a common method to deal with this phenomenon in soft tissue is water calibration, where a uniform water phantom is used to optimize the parameters in a high-order polynomial linearization algorithm. However, photoelectric interactions are also a significant contributor to x-ray attenuation in bone, thus water calibration is not sufficient. Typically, iterative bone correction algorithms are employed where bones are segmented in a first-pass image, then beam hardening from bones are corrected in the second-pass. However, beam hardening from materials others than water and bone, such as metal and contrast agent, become very difficult to correct. Even after application of the correction, conventional CT does not provide quantitative image values; instead, the same material at different locations often shows different CT numbers.

Another drawback of conventional CT is a lack of material characterization. For example, a highly attenuating material with a low density can result in the same CT number in the image as a less attenuating material with a high density. Thus, there is little or no information about the material composition of a scanned object based solely on the CT number.

BRIEF DESCRIPTION OF THE INVENTION

In one aspect, a method is provided for facilitating a reduction in artifacts. The method includes receiving data regarding a first energy spectrum of a scan of an object, and receiving data regarding a second energy spectrum of a scan of the object, wherein the second energy spectrum is different than the first energy spectrum. The method further includes reconstructing at least one original first energy image using the first energy spectrum data, reconstructing at least one original second energy image using the second energy spectrum data, transforming at least one original second energy image into at least one transformed first energy image, and combining at least one original first energy image with at least one transformed first energy image to generate a combined first energy image.

In another aspect, a method is provided for facilitating a reduction in artifacts. The method includes receiving first energy spectrum data for a scan of an object, and receiving second energy spectrum data for a scan of the object, wherein the second energy spectrum is different than the first energy spectrum. The method further includes reconstructing at least one original first energy image using the first energy spectrum data, reconstructing at least one original second energy image using the second energy spectrum data, transforming at least one original second energy image into at least one transformed first energy image, reprojecting at least one transformed first energy image to generate reprojected first energy spectrum data, and combining the first energy spectrum data with the reprojected first energy spectrum data to generate combined first energy spectrum data.

In yet another aspect, a multi-energy computed tomography (MECT) system is provided. The MECT system includes at least one radiation source, at least one radiation detector, and a computer operationally coupled to the at least one radiation source and the at least one radiation detector. The computer is configured to receive first energy spectrum data for a scan of an object, and receive second energy spectrum data for a scan of the object, wherein the second energy spectrum is different than the first energy spectrum. The computer is further configured to transform the second energy spectrum data into transformed first energy spectrum data, reconstruct at least one first energy image using the first energy spectrum data, reconstruct at least one transformed first energy image using the transformed first energy spectrum data, and combine at least one first energy image with at least one transformed first energy image to generate at least one combined first energy image.

A multi-energy computed tomography (MECT) system is provided. The MECT system includes at least one radiation source, at least one radiation detector, and a computer operationally coupled to the at least one radiation source and the at least one radiation detector. The computer is configured to receive first energy spectrum data for a scan of an object, and receive second energy spectrum data for a scan of the object, wherein the second energy spectrum is different than the first energy spectrum. The computer is further configured to transform the second energy spectrum data into transformed first energy spectrum data, and combine the first energy spectrum data with the transformed first energy spectrum data to generate combined first energy spectrum data.

DETAILED DESCRIPTION OF THE INVENTION

The methods and apparatus described herein address the synergistic combination of view aliasing artifact correction schemes and spectral-shift compensation algorithms to multiple energy computed tomography data acquired by sequential alteration of energy spectra. The output of the below described algorithm is non-aliased, spectral-shift compensated, high and low energy data (projections or reconstructed images) suitable for application of multi-energy decomposition algorithms.

Additionally, the methods described herein include novel approaches to make use of the basic properties of the x-ray and material interaction. For example, for each ray trajectory, multiple measurements with different mean x-ray energies are acquired. When Compton and photoelectric decomposition and/or basis material decomposition (BMD) are performed on these measurements, additional information is obtained that enables improved accuracy and characterization.

In some known CT imaging system configurations, an x-ray source projects a fan-shaped beam which is collimated to lie within an x-y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view." A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
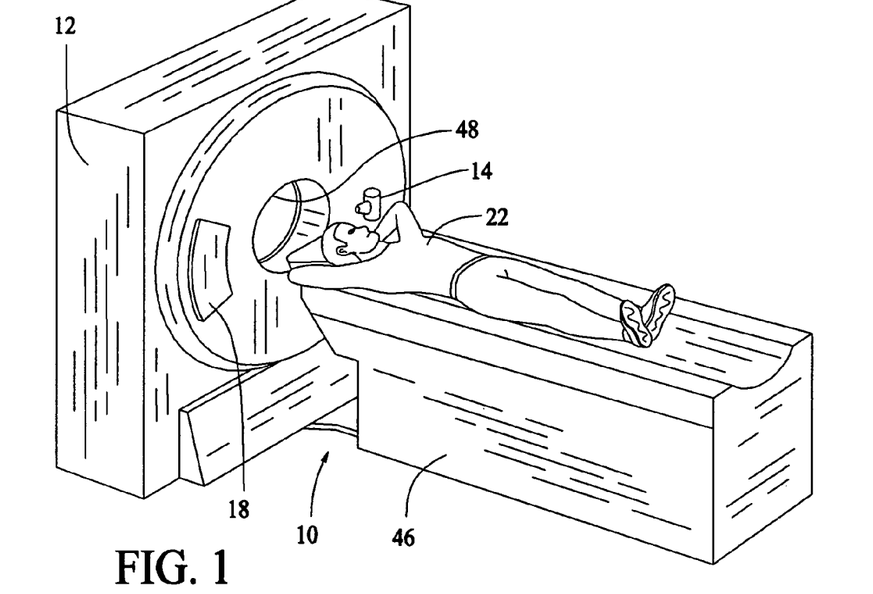
FIG. 1 is a pictorial view of a multi-energy computed tomography (MECT) imaging system.
Figure 2:
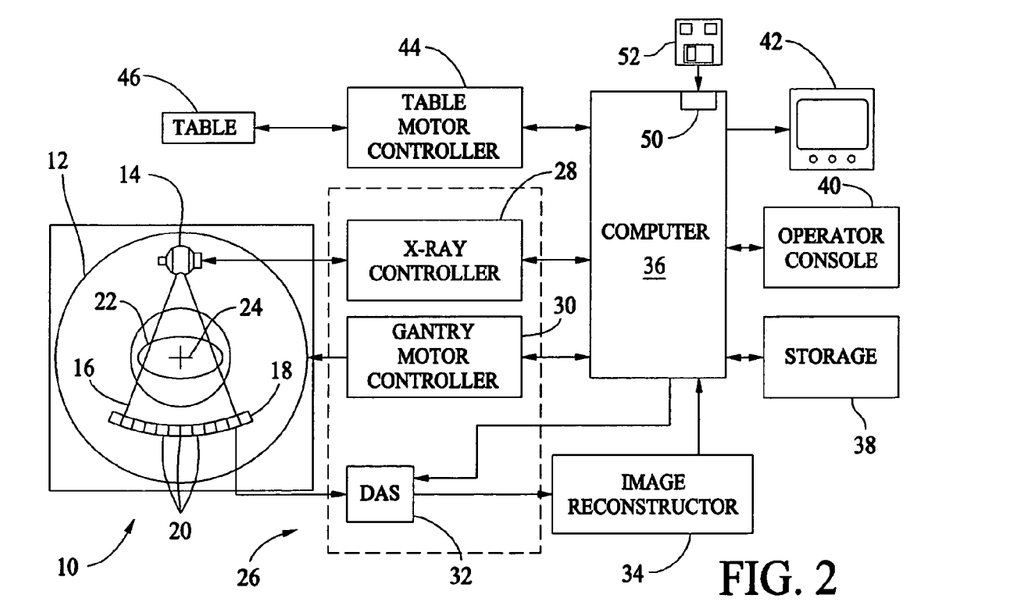
FIG. 2 is a block schematic diagram of the system illustrated in FIG. 1.

Referring to FIGS. 1 and 2, a multi-energy scanning imaging system, for example, a multi-energy, multi-slice computed tomography (MECT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of MECT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD, a MOD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

MECT system 10 is configured to be responsive to different x-ray spectra. MECT 10 facilitates reducing or eliminating a plurality of problems associated with conventional CT, such as, but not limited to, a lack of energy discrimination and material characterization. In the absence of object scatter, one only need system 10 to separately detect two regions of photon energy spectrum: the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation (1) Compton scatter and the (2) photoelectric effect. In order to characterize the behavior of an object under x-ray attenuation, only two independent parameters are measured. Thus, detected signals from two energy regions provide sufficient information to resolve the energy dependence of the object being imaged. Although the specific embodiment mentioned above refers to a third generation CT system, the methods described herein apply equally to fourth generation CT systems (stationary detector—rotating x-ray source) and fifth generation CT systems (stationary detector and x-ray source).

In an exemplary embodiment, MECT uses a decomposition algorithm, such as, but not limited to, a CT number difference algorithm, a Compton and photoelectric decomposition algorithm, a basis material decomposition (BMD) algorithm, and a logarithm subtraction decomposition (LSD) algorithm.

The CT number difference algorithm includes calculating a difference value in a CT or a Hounsfield number between two images obtained at different tube potentials. In one embodiment, the difference values are calculated on a pixel-by-pixel basis. In another embodiment, average CT number differences are calculated over a region of interest. The Compton and photoelectric decomposition algorithm includes acquiring a pair of images using MECT 10, and separately representing the attenuations from Compton and photoelectric processes. The BMD algorithm includes acquiring two CT images, wherein each image represents the equivalent density of one of the basis materials. Since a material density is independent of x-ray photon energy, these images are approximately free of beam-hardening artifacts. Additionally, an operator can choose the basis material to target a certain material of interest, thus enhancing the image contrast. In use, the BMD algorithm is based on the concept that the x-ray attenuation (in the energy region for medical CT) of any given material can be represented by proper density mix of other two given materials, accordingly, these two materials are called the basis materials. In one embodiment, using the LSD algorithm, the images are acquired with quasi-mono-energetic x-ray spectra, and the imaged object can be characterized by an effective attenuation coefficient for each of the two materials, therefore the LSD algorithm does not incorporate beam-hardening corrections. Additionally, the LSD algorithm is not calibrated, but uses a determination of the tissue cancellation parameters, which are the ratio of the effective attenuation coefficient of a given material at the average energy of each exposure. In an exemplary embodiment, the tissue cancellation parameter is primarily dependent upon the spectra used to acquire the images, and on any additional factors that change the measured signal intensity from that which would be expected for a pair of ideal, mono-energetic exposures.

It should be noted that in order to optimize a multi-energy CT system, the larger the spectra separation, the better the image quality. Also, the photon statistics in these two energy regions should be similar, otherwise, the poorer statistical region will dominate the image noise.

Figure 3:
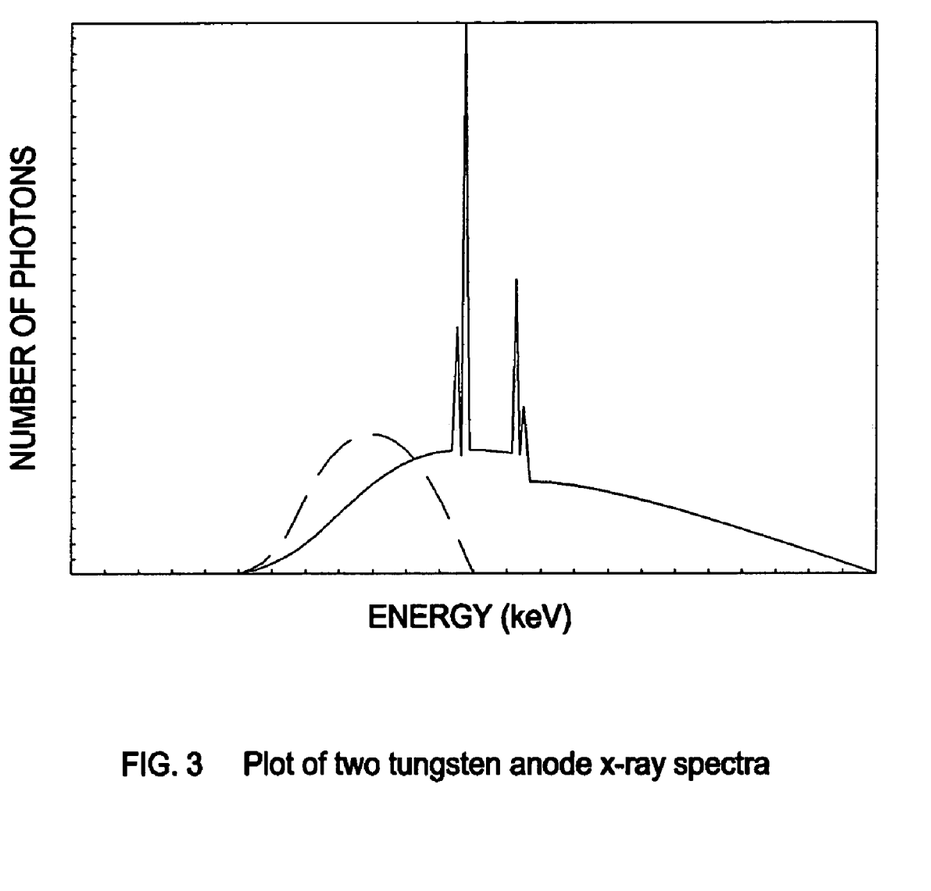
FIG. 3 illustrates a plot of different x-ray spectra.

Several methods for acquiring dual-energy computed tomography data have been proposed. Two scans, each using distinct x-ray spectra and covering the same anatomy, can be performed in series. Although this method can be implemented on standard CT systems without requiring hardware modifications, it presents some less than desirable effects. The finite time difference (approximately 0.3-0.5 seconds on current high-end third generation CT systems) between the scans creates the possibility that the patient's anatomical structures may move through either as a result of voluntary (e.g. musculoskeletal) or involuntary (e.g. cardiac or peristaltic) activity between the scans, resulting in misregistration artifacts in the images reconstructed by any suitable combination of the high and low energy data. Scanning at two different energies consecutively is also less than ideal since there is a substantial amount of spectrum overlap. This overlap is illustrated in FIG. 3. Furthermore, the exposure associated with scanning with two distinct spectra successively is approximately double, with much of the additional dose attributed to the lower kVp scan. Another method to acquire MECT data is to detect photon energy according to penetration depth at the detector. One drawback to this method is that the stopping of photons is statistical. Thus, there is still certain amount of energy spectra overlap. A third method for acquiring MECT data is photon counting. This method is optimal in that it provides clean spectra separation and an adjustable energy separation point for balancing photon statistics. Although detecting photon penetration depth and photon counting methods may be preferable since they are not as susceptible to patient motion artifacts and excessive patient dose, they cannot be implemented on current systems without completely replacing the x-ray detector assembly.

Another method of acquiring multiple energy computed tomography data involves sequentially changing the energy spectrum between the higher and lower energies during a single scan. This sequential alternating of beam energy can be accomplished by inserting a spin filter, having at least two materials with different attenuation properties, in front of the x-ray source. This method does not require changes to the detector, yet now modifications to the tube-side filtering assembly and control should be implemented. A similar effect can be accomplished by sequentially changing the output of the high-voltage supply that powers the x-ray tube. kV modulation may require modification of the x-ray generator control circuitry in the form of firmware and/or hardware changes, but does not necessitate detector or tube filter reengineering. Covering alternating slits of the detector collimator with thin metal foil will also achieve a similar effect. This requires minimally invasive engineering changes to the detector collimator, but does not allow the system to be readily converted between single and dual-energy scanning modes, and may result in increase dose to the patient. With that in mind, one embodiment of the present invention utilizes modulation of the high-voltage supply. It should be noted that this kV modulation can be coupled with modulation of the tube current. The mA modulation typically occurs at a much lower frequency than the kV modulation due to the physical (e.g. thermal) limitations on the filament.

All three of these multi-energy data acquisition techniques-spin filtering, modulating kV, and alternating filtration with detector cell location along the detector arc-are advantageous in many ways. First, the time interval between acquisitions along ray paths of approximately equivalent angles can be reduced by more than two orders of magnitude. A high-frequency (HF) generator kV response time, that is, the time needed to reach a set voltage, is approximately 250 μs for closed-loop voltage control designs. It is then possible to create projection interleaving with every other view, every second view, or any other appropriate modulation function. This invention will assume heretofore that the dual energy data is interleaved with every other view. Although this reduces misregistration artifacts by inherently registering the low and high-energy acquisitions in time, the temporal resolution for a scan does not change. Images reconstructed from this data still require a minimal projection set covering 180°+2 $\gamma_m$, where 2 $\gamma_m$ is the detector fan angle. In some cases, involuntary or voluntary patient motion may still cause inconsistency between data at the beginning and end of the scan, resulting in motion artifacts, such as streaking, doubling, or blurring. Although not specific to this method of data acquisition, temporal resolution considerations are noted here to differentiate between intrascan and interscan artifacts in multi-energy scanning. Another advantage to kV-modulated acquisition is the reduction in patient dose. Compared to acquiring projection data sets at different energies one after another, interleaved acquisition could realize at least a 50% reduction in exposure.

However, this manner of acquisition is not without penalty. By sequentially changing the energy spectrum between the higher and lower energies during a single scan, the total of number of projections acquired remains constant, but is now divided among two energies. Therefore, if every other view is collected at an alternate energy, there are half as many projections for each energy spectrum. Without an adequate number of projections, aliasing occurs.

According to the Shannon sampling theorem, the original data must be sampled at a rate of at least twice the highest spatial frequency contained in the signal to avoid aliasing. View aliasing artifacts can be seen as streaks in reconstructed images. Theoretically, the minimum sampling frequency in the azimuthal direction for equiangular fan beam geometry is given by $$N_{\min} = \frac{4\pi R v_m}{1 - \sin\gamma_m}$$

where, $N_{min}$ is the minimum number of views, R is the radius of the artifact free zone of reconstruction, $v_m$ is the maximum resolvable spatial frequency, and $\gamma_m$ is half the detector fan angle. By interleaving the MECT acquisition data using ultrafast kV modulation, the same number of total views collected per rotation is maintained, but the number of views collected at each energy is reduced. This problem gets progressively worse as the number of energies increases. For the case of dual energy CT, modulating the kVp with every other view halves the number of projections collected for each spectra. From the above equation, it is apparent that if the number of projections collected in 360° is halved, then the radius of the artifact-free zone will be reduced by 50% if the desired maximum resolvable frequency remains fixed. Similarly, halving the number of projections will result in halving the maximum resolvable frequency in the same field of view (FOV) radius. For scans focusing on small FOVs, such as cardiac or head studies, this may have less significant impact.

In practice, the above equation is not strictly satisfied. Rather, a variety of methods are used to minimize the conspicuity of view aliasing artifacts. One of these such methods is the quarter-detector offset. By offsetting the detector array by exactly one-quarter of the width of a detector element, conjugate views, or those views 180° apart, will have rays that are slightly shifted. This setup provides the additional data needed to minimize view aliasing artifacts. In addition to hardware geometry, there are many software techniques for suppressing view aliasing effects. In general, any sort of smoothing algorithm will be beneficial for reducing aliasing artifact conspicuity. However, high-frequency image components are sacrificed with such low-pass filtering techniques. A number of pre-reconstruction interpolation schemes also exist, as well. These techniques include view interpolation, interpolation in Radon space, and interpolation in the Fourier domain. These interpolation schemes may be simple linear or bilinear algorithms, higher order algorithms using Laguerre polynomials, or more complicated adaptive schemes. In addition, a number of reprojection based methods have been proposed to alleviate the effects of view aliasing, such as, but not limited to, intermediate view reprojection (IVR), intermediate view deconvolved-reprojection (IDVR), error correction (EC), and hybrid schemes. These methods are typically described in terms of view-aliased, single-energy computed tomography (SECT) scans; however, they could readily be applied separately for each set of view-aliased ME projections. Although this would provide some reduction in artifact conspicuity in reconstructed images, only sub-optimal results are realized. Furthermore, the fundamental limitation of kV-modulated MECT remains, the final multi-energy decomposition images will have voxels for which only one energy of data was acquired the data from the other energy (ies) lies in the 'missing' views. Herein described are methods and apparatus configured such that the interleaved multiple energy data can be utilized in a manner that is mutually advantageous to solve this problem.

A method for the synergistic combination of view aliasing artifact correction schemes and spectral-shift compensation algorithms and its application to multiple energy computed tomography data acquired by the sequential alteration of energy spectra is provided below. The output of this algorithm is non-aliased, spectral-shift compensated, high and low energy data (projections or reconstructed images) suitable for application of multi-energy decomposition algorithms.

Additionally, a method to utilize kV-modulated multiple energy projection data to perform simultaneous spectral-shift compensation and view-aliasing artifact reduction is provided. The herein described methods are implementable in first, second, third, and fourth generation CT systems having single-tube/single-detector systems as well as multiple-tube/multiple-detector systems and other multiple-tube/multiple-detector systems or volume CT methods. Application is also possible in a dedicated breast CT system. The herein described methods and apparatus can be applied to any clinical application benefiting from multiple energy CT, including fat/lean tissue characterization, physics-based segmentation, multiple contrast discrimination, and bone mineral densitometry. The herein described methods and apparatus can equally be applied to non-destructive testing applications, including explosive and contraband detection.

Figure 4:
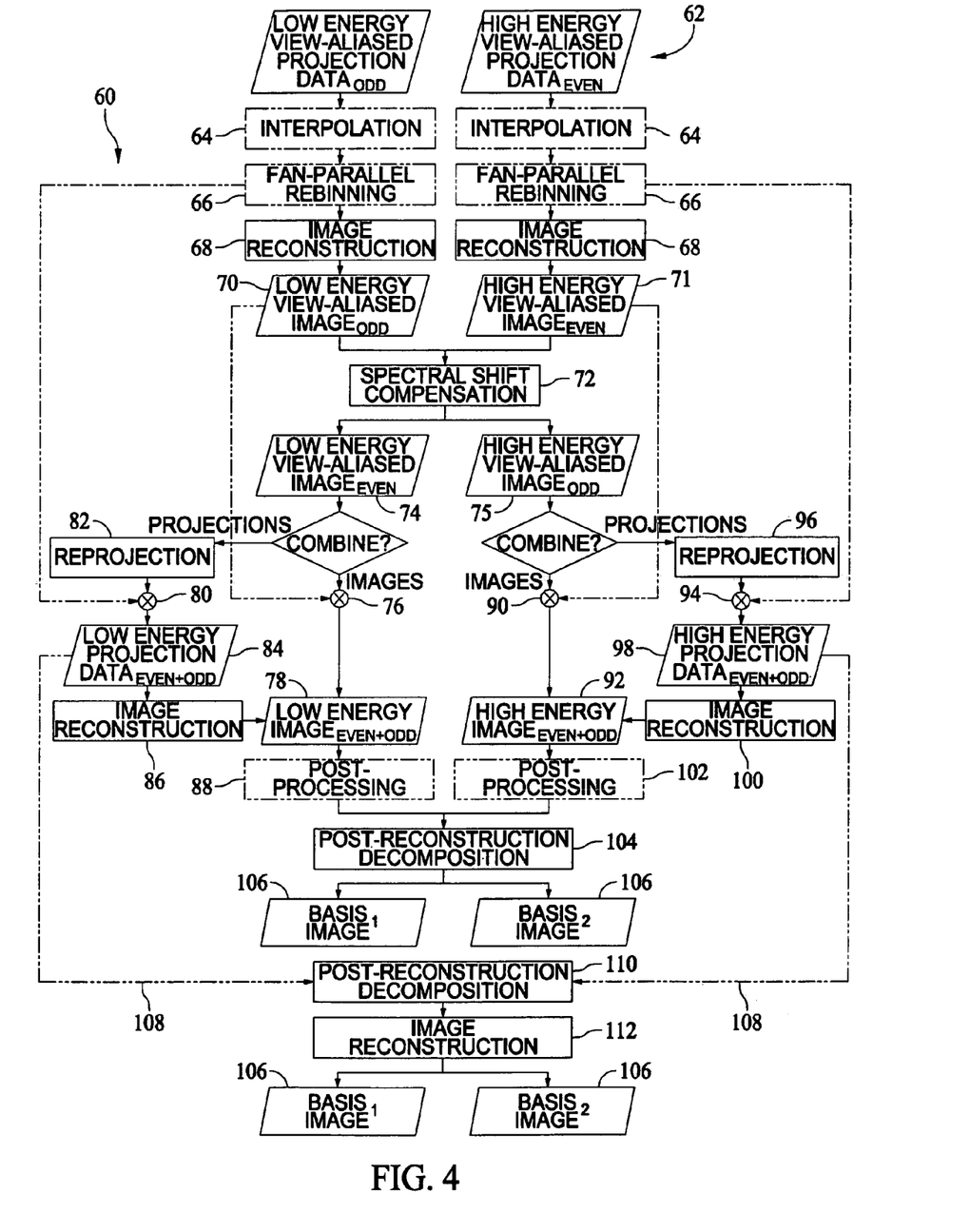
FIG. 4 illustrates a image-based method of facilitating a reduction in artifacts.
Figure 5:
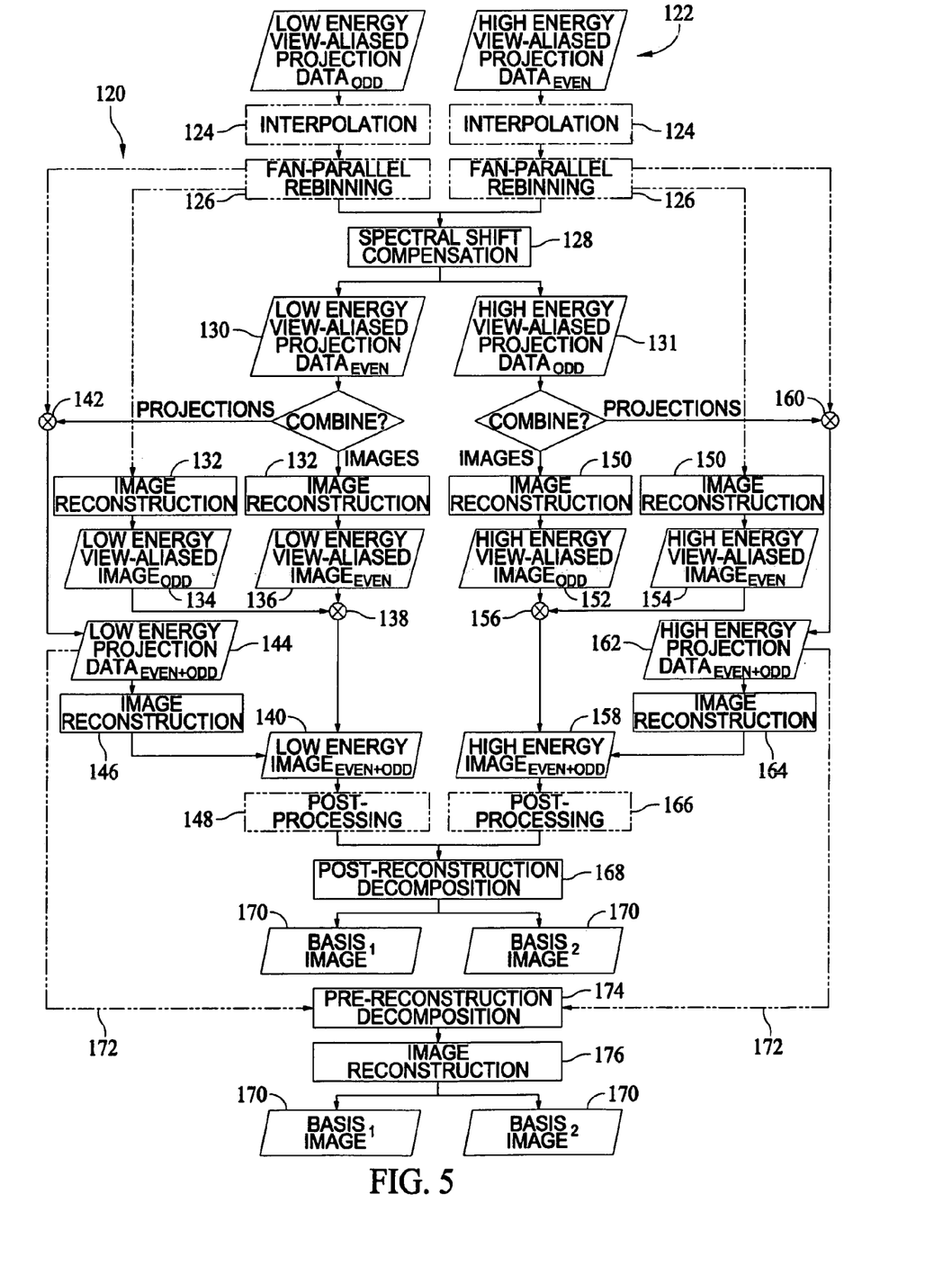
FIG. 5 illustrates an projection-based method of facilitating a reduction in artifacts.

Herein two methods for facilitating a reduction in artifacts are described and shown in FIG. 4 and FIG. 5. Traditional methods of spectral-shift compensation operate on reconstructed image data. However, the availability of MECT data also facilitates spectral-shift compensation algorithms to be applied in the projection domain. FIG. 4 illustrates an image-based method 60 of facilitating a reduction in artifacts. Although method 60 is described in the context of a dual-energy CT, method 60 is extendable to MECT applications including applications using three or more energy spectra. Method 60 includes acquiring interleaved dual energy projection data 62 such that even and odd views are at high and low energies, respectively. Note that the assignment of high and low energies to even and odd views can be inverted without affecting the algorithm. Additionally, as stated above, the interleaving need not be every other view. In general, the interleaving can be every n views, where n is greater or equal to one and less than one half of the total number of views obtained. It should be noted that the established minimum angular range requirements placed on a non-kV-interleaved projection set used for halfscan and fullscan image reconstruction techniques still apply for of kV-interleaved projection set. Standard gain, offset, afterglow, detector temperature, primary beam intensity, and other deterministic error corrections are conducted on the projection data sets, using kV-dependent calibrations where applicable. This data can be acquired in helical or axial mode, using fan or cone beam geometries, gated (prospectively or retrospectively), or ungated.

Method 60 optionally includes interpolating 64 the missing views of the projection data 62, and optionally rebinning 66 the fan-beam projection data sets to an equivalent parallel-beam projection data set. Method 60 also includes reconstructing 68 low and high-energy cross-sectional images 70 and 71, respectively, using a known reconstruction technique. For example, filtered-back projection (FBP), algebraic reconstruction techniques (ART), and/or simultaneous algebraic reconstruction techniques (SART) can be used. Typically, ART algorithms are used to reconstruct limited view projection sets, but tend to be computationally inefficient. Halfscan or fullscan reconstructions can be applied. Since images 70 are reconstructed 68 using an incomplete set of views, aliasing artifacts will be present, especially in the periphery of the scan field of view (SFOV).

Method 60 further includes spectral-shift compensating 72 using the view-aliased low and high-energy images 70 and 71, respectively, wherein any number of spectral-shift compensation algorithms can be applied. The spectral-shift compensation algorithms include calibration-based methods or may utilize any number of single-pass or iterative beam hardening algorithms, including multi-energy basis energy decomposition. The goal of this step is to utilize the dual energy images to determine the effective attenuation at the energies used to acquire the high and low energy datasets. Once the effective attenuation at any desired energy is determined, the low energy image 70 (reconstructed from odd projections) is transformed into a high-energy image 75 (at odd projections). Similarly, the high-energy image 71 (reconstructed from even projections) is transformed into a low energy image 74 (at even projections). Therefore, low and high-energy images sampled at all projection angles are obtained. In other words, a scan of an object is performed using two or more different energy spectra and a plurality of original first energy images and a plurality of second energy images is generated based upon data received from the scan. The original first energy images are transformed into a plurality of second energy images as described herein. Additionally, the original second energy images are transformed into a plurality of first energy images. In one embodiment, and as described below, the original first energy images and the transformed first energy images are combined to form a complete set of view-aliasing-artifact-compensated first energy images.

More specifically, in one embodiment, method 60 includes combining 76 the low energy image at even projections 74 with the low energy image at odd projections 70 to create a complete set of low energy image data 78. In an alternative embodiment, method 60 includes combining 80 even and odd low energy data in projection space. More specifically, the transformed low energy images 74 (reconstructed from even projections) are reprojected 82 into Radon space and combined 80 with the original low energy projections (at odd projections) to create a complete-set (both odd and even projections) of view-aliasing-artifact-compensated projection data 84 at the low energy. In one embodiment, as an alternative to method step 76, an image reconstruction 86 is performed on the complete set of low energy projection data 84 to create the complete set of low energy image data 78. Method 60 may optionally include performing a post-processing 88 on the complete set of low energy image data 78, such as, but not limited to, noise reduction and edge enhancement.

In one embodiment, method 60 includes combining 90 the high energy image (reconstructed from even projections) with the high energy image at odd projections to create a complete set of high energy image data 92. In an alternative embodiment, method 60 includes combining 94 even and odd high energy data in projection space. More specifically, the transformed high energy images 75 (reconstructed from even projections) are reprojected 96 into Radon space and combined 94 with the original high energy projections (at even projections) to create a complete-set (both odd and even projections) of view-aliasing-artifact-compensated projection data 98 at the high energy. In one embodiment, as an alternative to method step 90, an image reconstruction 100 is performed on the complete set of high energy projection data 98 to create the complete set of high energy image data 92. Method 60 may optionally include performing a post-processing 102 on the complete set of high energy image data 92, such as, but not limited to, noise reduction and edge enhancement. In one embodiment, the complete set of high energy image data 92 and the complete set of low energy image data 78 are then input to a post-reconstruction decomposition 104, and the resulting basis material images 106 are then available for optional post-processing and display to the observer.

In an alternative embodiment, the complete set of high energy projection data 98 and the complete set of low energy projection data 84 are input 108 into a pre-reconstruction MECT decomposition algorithm 110 and then reconstructed 112. The resulting basis material images 106 are then available for optional post-processing and display to the observer.

With regard to image reconstruction, if the image reconstruction process is linear, such as a FBP algorithm, it follows that a combination of images reconstructed from odd and even projections, respectively, is equivalent to combining odd- and even-sampled projections followed by a reconstruction of the complete data set.

FIG. 5 illustrates another embodiment of a method 120 for facilitating a projection-based method of artifact reduction. Although method 120 is described in the context of a dual-energy CT, method 120 is extendable to MECT applications including applications using three or more energy spectra. Method 120 includes acquiring interleaved dual energy projection data 122 such that even and odd views are at high and low energies, respectively. Note that the assignment of high and low energies to even and odd views can be inverted without affecting the algorithm. Additionally, as stated above, the interleaving need not be every other view. In general, the interleaving can be every n views, where n is greater or equal to one and less than one half of the total number of views obtained. It should be noted that the established minimum angular range requirements placed on a non-kV-interleaved projection set used for halfscan and fullscan image reconstruction techniques still apply for of kV-interleaved projection set. Standard gain, offset, afterglow, detector temperature, primary beam intensity, and other deterministic error corrections are conducted on the projection data sets, using kV-dependent calibrations where applicable. This data can be acquired in helical or axial mode, using fan or cone beam geometries, gated (prospectively or retrospectively), or ungated.

Method 120 optionally includes interpolating 124 the missing views of the projection data 122, and optionally rebinning 126 the fan-beam projection data sets to an equivalent parallel-beam projection data set. Method 120 also includes spectral-shift compensating 128 using the view-aliased low and high-energy projection data, 130 and 131, respectively, wherein any number of spectral-shift compensation algorithms can be applied. The spectral-shift compensation algorithms include calibration-based methods or may utilize any number of single-pass or iterative beam hardening algorithms, including multi-energy basis energy decomposition. The goal of this step is to utilize the dual energy projection data to determine the effective attenuation at the energies used to acquire the high and low energy datasets. Once the effective attenuation at any desired energy is determined, the low energy projection data (at odd projections) is transformed into high-energy projection data 131 (at odd projections). Similarly, the high-energy projection data (at even projections) is transformed into low energy projection data 130 (at even projections). Therefore, low and high-energy projection data sampled at all projection angles are obtained.

In one embodiment, method 120 includes reconstructing 132 the even low energy projection data and the original odd low energy projection data to produce a low energy image at odd projections 134 and a low energy image at even projections 136, and combining 138 the low energy image at even projections 136 with the low energy image at odd projections 134 to create a complete set of low energy image data 140. Reconstruction 132 is performed using a known reconstruction techniques. For example, filtered-back projection (FBP), algebraic reconstruction techniques (ART), and/or simultaneous algebraic reconstruction techniques (SART) can be used. Typically, ART algorithms are used to reconstruct limited view projection sets, but tend to be computationally inefficient. Halfscan or fullscan reconstructions can be applied. Since images 134 and 136 are reconstructed 132 using an incomplete set of views, aliasing artifacts will be present, especially in the periphery of the scan field of view (SFOV).

In an alternative embodiment, method 120 includes combining 142 the even low energy projection data and the original odd low energy projection data to create a complete-set (both odd and even projections) of view-aliasing-artifact-compensated projection data 144 at the low energy. In one embodiment, as an alternative to method step 138, an image reconstruction 146 is performed on the complete set of low energy projection data 144 to create the complete set of low energy image data 140. Method 120 may optionally include performing a post-processing 148 on the complete set of low energy image data 140, such as, but not limited to, noise reduction and edge enhancement.

In one embodiment, method 120 includes reconstructing 150 the odd high energy projection data and the original even high energy projection data to produce a high energy image at odd projections 152 and a high energy image at even projections 154, and combining 156 the high energy image at even projections 154 with the high energy image at odd projections 152 to create a complete set of high energy image data 158. Reconstruction 150 is performed using a known reconstruction techniques. For example, filtered-back projection (FBP), algebraic reconstruction techniques (ART), and/or simultaneous algebraic reconstruction techniques (SART) can be used. Typically, ART algorithms are used to reconstruct limited view projection sets, but tend to be computationally inefficient. Halfscan or fullscan reconstructions can be applied. Since images 152 and 154 are reconstructed 150 using an incomplete set of views, aliasing artifacts will be present, especially in the periphery of the scan field of view (SFOV).

In an alternative embodiment, method 120 includes combining 160 the odd high energy projection data and the original even high energy projection data to create a complete-set (both odd and even projections) of view-aliasing-artifact-compensated projection data 162 at the high energy. In one embodiment, as an alternative to method step 156, an image reconstruction 164 is performed on the complete set of high energy projection data 162 to create the complete set of high energy image data 158. Method 120 may optionally include performing a post-processing 166 on the complete set of high energy image data 158, such as, but not limited to, noise reduction and edge enhancement. In one embodiment, the complete set of high energy image data 158 and the complete set of low energy image data 140 are then input to a post-reconstruction decomposition 168 and the resulting basis material images 170 are then available for optional post-processing and display to the observer.

In an alternative embodiment, the complete set of high energy projection data 162 and the complete set of low energy projection data 144 are input 172 into a pre-reconstruction MECT decomposition algorithm 174 and then reconstructed 176. The resulting basis material images 170 are then available for optional post-processing and display to the observer.

With regard to image reconstruction, if the image reconstruction process is linear, such as a FBP algorithm, it follows that a combination of images reconstructed from odd and even projections, respectively, is equivalent to combining odd- and even-sampled projections followed by a reconstruction of the complete data set.

It should be noted that method 60 and method 120 are two ways of combining interleaved multi-energy data to perform minimization of beam hardening and view-aliasing artifacts. These or other similar methods, or portions thereof, can be extended using iterative techniques.

Note that the selection between method 60 and method 120 follows appropriate evaluation of necessary system tradeoffs, such as processing time, memory requirements, and algorithm performance and consideration of the specific requirement of the imaging or diagnostic task. For example, a particular diagnostic task may require the display of CT images in addition the basis material images. The selection between method 60 and method 120 determines the immediate availability, type, and quality of output CT images.

Note that the above-described techniques also require an optimization between the number of views acquired and the number of energies used. To acquire high spatial resolution images, one would desire a minimal view aliasing, and minimal number of energy levels in the acquisition. To optimize the beam hardening correction and tissue characterization one would require as many different energy acquisitions as possible. Thus, the same general approach can be taken, but the modulation and correction scheme can be varied to suit the specific requirement of the imaging or diagnostic task.

While the invention has been described in terms of various specific embodiments, those skilled in the art will recognize that the invention can be practiced with modification within the spirit and scope of the claims.

What is claimed is:

1. A method for facilitating a reduction in artifacts, said method comprising:
   receiving data regarding a scan of an object, the data corresponding to a plurality of sequential projections comprising a first set of projections corresponding to a first energy spectrum and a second set of projections corresponding to a second energy spectrum, the first set of projections interleaved with the second set of projections;
   reconstructing at least one original first energy image using the data corresponding to the first set of projections;
   reconstructing at least one original second energy image using the data corresponding to the second set of projections;
   transforming at least one original first energy image into at least one transformed second energy image;
   transforming at least one original second energy image into at least one transformed first energy image;
   combining at least one original first energy image with at least one transformed first energy image to generate at least one combined first energy image; and
   combining at least one original second energy image with at least one transformed second energy image to generate at least one combined second energy image.

2. A method in accordance with claim 1 further comprising decomposing the combined first and second energy images to generate at least one quantitative material characterization image.

3. A method in accordance with claim 2 wherein said decomposing comprises at least one of decomposing by a Compton and photoelectric decomposition, decomposing by a basis material decomposition (BMD), and decomposing by a logarithm subtraction decomposition (LSD).

4. A method in accordance with claim 1 wherein said receiving data comprises receiving data comprising fan-beam projection data, said method further comprising rebinning the fan-beam projection data into equivalent parallel-beam projection data.

5. A method for facilitating a reduction in artifacts, said method comprising:
   receiving data from a scan of an object, the data corresponding to a plurality of sequential projections comprising a first set of projections corresponding to a first energy spectrum and a second set of projections corresponding to a second energy spectrum, the first set of projections interleaved with the second set of projections;
   reconstructing at least one original first energy image using the data corresponding to the first set of projections;
   reconstructing at least one original second energy image using the data corresponding to the second set of projections;
   transforming at least one original first energy image into at least one transformed second energy image;
   transforming at least one original second energy image into at least one transformed first energy image;
   reprojecting at least one transformed first energy image to generate reprojected first energy spectrum data;
   reprojecting at least one transformed second energy image to generate reprojected second energy spectrum data;
   combining the first energy spectrum data with the reprojected first energy spectrum data to generate combined first energy spectrum data; and
   combining the second energy spectrum data with the reprojected second energy spectrum data to generate combined second energy spectrum data.

6. A method in accordance with claim 5 further comprising decomposing the combined first energy spectrum data and the combined second energy spectrum data to generate at least one quantitative material characterization image.

7. A method in accordance with claim 6 wherein said decomposing comprises at least one of decomposing by a Compton and photoelectric decomposition, decomposing by a basis material decomposition (BMD), and decomposing by a logarithm subtraction decomposition (LSD).

8. A method in accordance with claim 5 further comprising reconstructing at least one combined first energy image using the combined first energy spectrum data.

9. A method in accordance with claim 8 further comprising reconstructing at least one combined second energy image using the combined second energy spectrum data.

10. A method in accordance with claim 9 further comprising decomposing the combined first and second energy images to generate at least one quantitative material characterization image.

11. A method in accordance with claim 10 wherein said decomposing comprises at least one of decomposing by a Compton and photoelectric decomposition, decomposing by a basis material decomposition (BMD), and decomposing by a logarithm subtraction decomposition (LSD).

12. A multi-energy computed tomography (MECT) system comprising:
   at least one radiation source configured to sequentially change the energy spectrum of the radiation between a higher energy and a lower energy during a single scan by sequentially alternating the source energy;
   at least one radiation detector; and
   a computer operationally coupled to said at least one radiation source and said at least one radiation detector, said computer configured to:
   receive data from a scan of an object, said data corresponding to a plurality of sequential projections comprising a first set of projections corresponding to a first energy spectrum and a second set of projections corresponding to a second energy spectrum, said first set of projections interleaved with said second set of projections;
   transform said data corresponding to said first set of projections into transformed second energy spectrum data;
   transform said data corresponding to said second set of projections into transformed first energy spectrum data;
   reconstruct at least one first energy image using said data corresponding to said first set of projections;
   reconstruct at least one second energy image using said data corresponding to said second set of projections;
   reconstruct at least one transformed first energy image using said transformed first energy spectrum data;
   reconstruct at least one transformed second energy image using said transformed second energy spectrum data;
   combine at least one first energy image with at least one transformed first energy image to generate at least one combined first energy image; and
   combine at least one second energy image with at least one transformed second energy image to generate at least one combined second energy image.

13. An MECT system in accordance with claim 12, wherein said computer further configured to decompose said combined second energy image and said combined first energy image to generate at least one quantitative material characterization image.

14. An MECT system in accordance with claim 13, wherein said computer configured to decompose at least one combined second energy image using at least one of a Compton and photoelectric decomposition, a basis material decomposition (BMD), and a logarithm subtraction decomposition (LSD).

15. A multi-energy computed tomography (MECT) system comprising:
   at least one radiation source;
   at least one radiation detector; and
   a computer operationally coupled to said at least one radiation source and said at least one radiation detector, said computer configured to:
   receive data from a scan of an object, said data corresponding to a plurality of sequential projections comprising a first set of projections corresponding to a first energy spectrum and a second set of projections corresponding to a second energy spectrum, said first set of projections interleaved with said second set of projections;
   transform said data corresponding to said first set of projections into transformed second energy spectrum data;
   transform said data corresponding to said second set of projections into transformed first energy spectrum data;
   combine said first energy spectrum data with said transformed first energy spectrum data to generate combined first energy spectrum data; and
   combine said second energy spectrum data with said transformed second energy spectrum data to generate combined second energy spectrum data.

16. An MECT system in accordance with claim 15, wherein said computer further configured to decompose said combined first energy spectrum data and said combined second energy spectrum data to generate at least one quantitative material characterization image.

17. An MECT system in accordance with claim 16, said computer configured to decompose said combined first and second energy spectrum data using at least one of a Compton and photoelectric decomposition, a basis material decomposition (BMD), and a logarithm subtraction decomposition (LSD).

18. An MECT system in accordance with claim 15, wherein said computer further configured to reconstruct at least one combined first energy image using said combined first energy spectrum data.

19. An MECT system in accordance with claim 18, wherein said computer further configured to reconstruct at least one combined second energy image using said combined second energy spectrum data.

20. An MECT system in accordance with claim 19, wherein said computer further configured to decompose said combined first energy image and said combined second energy image to generate at least one quantitative material characterization image.

21. An MECT system in accordance with claim 20, wherein said computer configured to decompose said combined first and second energy images using at least one of a Compton and photoelectric decomposition, a basis material decomposition (BMD), and a logarithm subtraction decomposition (LSD).

* * * * *